United States Patent [19]
Simmons

[11] Patent Number: 5,131,386
[45] Date of Patent: Jul. 21, 1992

[54] TESTICLE SUPPORT MEANS

[76] Inventor: Gregory C. Simmons, 1 Simmons Dr., Shelburne, Vt. 05482

[21] Appl. No.: 671,096

[22] Filed: Mar. 18, 1991

Related U.S. Application Data

[63] Continuation-in-part of Ser. No. 204,413, Jun. 8, 1988, Pat. No. Des. 323,398.

[51] Int. Cl.⁵ .............................................. A61F 5/40
[52] U.S. Cl. ........................................ 602/70; 2/401
[58] Field of Search .............................. 128/158–161, 128/168; 2/401, 403–405

[56] References Cited

U.S. PATENT DOCUMENTS

| | | | |
|---|---|---|---|
| 1,474,927 | 11/1923 | Cawthra | 128/158 |
| 2,294,066 | 8/1942 | Bachler | 128/158 |
| 2,576,024 | 11/1951 | Laser | 128/157 |
| 3,176,686 | 4/1965 | Barnes | 128/158 |
| 3,497,872 | 3/1970 | Mitchell | 2/2 |
| 3,936,075 | 2/1976 | Jeliffe | 280/150 |
| 4,487,202 | 12/1984 | Sachse | 128/158 |
| 4,590,931 | 5/1986 | Kidwell, Jr. | 128/162 |
| 4,955,088 | 9/1990 | Terjesen | 2/403 |

Primary Examiner—David Isabella
Assistant Examiner—Gina Gualtieri
Attorney, Agent, or Firm—Cohen, Pontani, Lieberman & Pavane

[57] ABSTRACT

The means comprises a support insert pad protruding inward within the crotch portion of any men's garments that are worn next to the skin. The support insert pad is positioned to be behind the testicles of the male to provide a lifting and support platform for the testicles while allowing for the rest of the garment to hold the genitals stable against the body. The shape of the insert support pad is in a crescent form that fits the vacant area behind the user's scrotum.

10 Claims, 1 Drawing Sheet

TESTICLE SUPPORT MEANS

This application is a continuation-in-part of the earlier filed application, Ser. No. 07/204,413 filed on Jun. 8, 1988, now U.S. Pat. No. Do.323398.

FIELD OF THE INVENTION

This invention pertains to testicle support means, and in particular to such testicle support means provided by wearing apparel, specifically wearing apparel that covers the crotch portion and passes between the legs of the user.

BACKGROUND OF THE INVENTION

Testicle support is well known and a necessary function in athletic and medical situations. It is known in the art that a testicle support comprises two important processes. The first is to elevate or pull the user's testicles forward and out from between the user's legs and the second is to hold the testicles in place. The prior art uses these processes either individually or in conjunction.

Examples of these type devices include U.S. Pat. No. 2,294,006 issued to Baehler on Aug. 25, 1942, ("Bachler") for a "Suspensory" and U.S. Pat. No. 4,487,202 issued to Sachse on Dec. 11, 1984 ("Sachse") for "Testic Support For Elevating and Treating Diseased Testes and Epididymides". The general function of these references and a number of others in the art is to get behind and under the testes and scrotum,, to move the testes forward and out from between the legs and to anchor testes out of the way. The Baehler reference uses loops to accomplish this goal. However, these references are limited as to the garment they could be used with and also as to that it would be fairly uncomfortable to be used in everyday situations.

Clearly, it is desirable to have a testicle support means and a method of providing testicle support that can be used comfortably in all situations with a number of different garments. It is the object of the invention, then to set forth a testicle support means which avoids the disadvantages and limitations, above-recited, which were obtained in prior testicle supports. It is also the object of this invention to teach a testicle support means that can be positioned or sewn into any men's garments to be worn directly next to the skin in the crotch area. Another object of this invention is to teach a noval means of contacting the perineum and the posterior portion of the user's scrotum and testicles in order to provide a mean for testicle support.

It is also the object of this invention to teach a method of providing testicle support that is simple to use and that will enable the user to comfortably maintain this support for extended periods of time.

SUMMARY OF THE INVENTION

Particularly it is the object of this invention to set forth a testicle support means, for use in men's garments worn next to the skin, comprising a male garment. The male garment comprises a first means for surrounding the lower trunk of the user's body, a second means for surrounding at least part of each of the user's legs separately, and a connection means. The connection means, comprises fabric material for covering the crotch portion of the user and for connecting, the first means and the second means. The connection means has a pad support means which comprises a crescent-shaped form of flexible material attached to the connection means for contacting the perineum and the posterior portion of the user's scrotum. The crescent-shaped form has a center section; the crescent-shaped form further has twin end sections. The crescent-shaped form further has a center section with a thicker cross-sectional dimension, and twin end sections having a thinner cross-sectional dimension.

Further objects and features of this invention will become more apparent by reference to the following description taken in conjunction with the accompanying figures;

DETAILED DESCRIPTION OF THE PREFERRED EMBODIMENT

Figure 1:
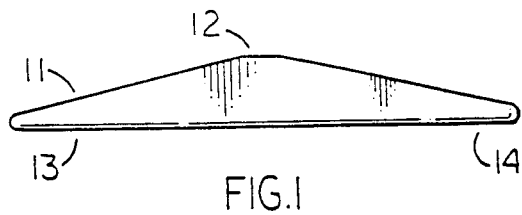
FIG. 1 is an frontal view of the novel testicle support means.
Figure 2:
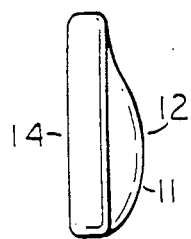
FIG. 2 is a side view thereof.
Figure 3:
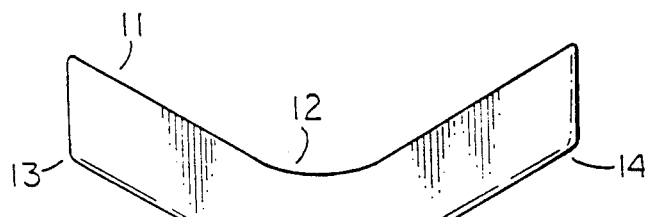
FIG. 3 is a top view thereof.
Figure 4:
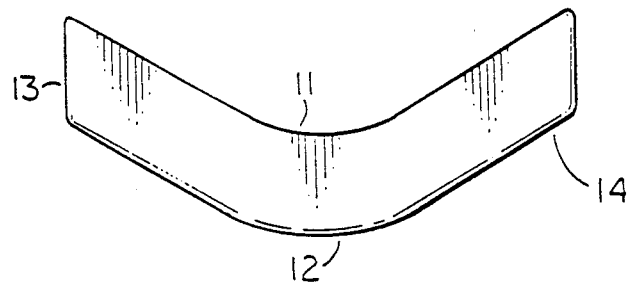
FIG. 4 is a bottom view thereof.
Figure 5:
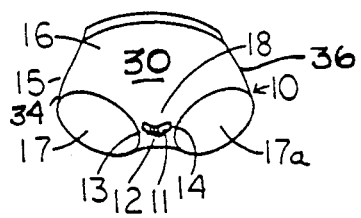
FIG. 5 is a perspective view of the novel support mas in position in men's briefs.
Figure 6:
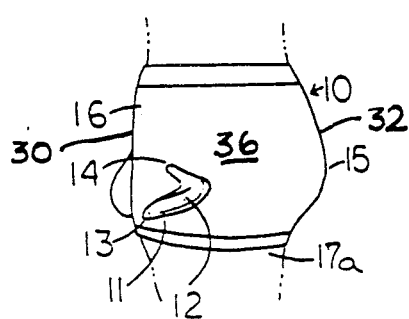
FIG. 6 is a side perspective view of the novel support menas in position behind the user's scrotum in men's briefs.
Figure 7:
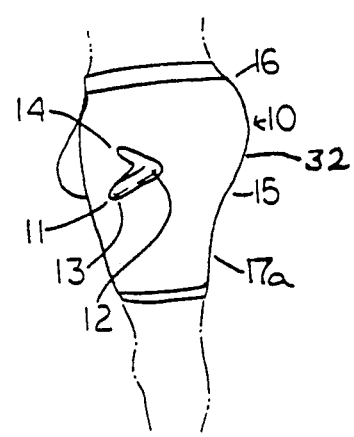
FIG. 7 is a side elevational view of the novel support means in position in long leg apparel.

As shown in the figures, the testicle support means 10 comprises an insert 11 that is formed in a crescent or winged shape. The insert 11 has a thickened center section 12 and twin end sections 13 and 14. The insert is cut from a flexible foam material, or the like, to a predetermined shape. The insert 1 is then positioned in men's briefs 15, shorts a swimsuit, or the like. The garment 15 has trunk covering or encircling portion 16, having a front 30, a back 32 and two sides 34 and 36. A connector piece or crotch panel 18 connects the front and back of the trunk covering portion 16 and with sides 34 and 36, defines the leg covering portions 17 and 17a of the garment 15. The insert 11 is attached to the connection piece or crotch panel 18. The insert 11 is sewn or glued into position in the garment 15 in the crotch area 18, so that when the garment is worn the insert will be located behind the male's testicles, so that the small vacant area behind the testicles is filled by the insert 11. The insert 11 is adapted to straddle and be in contact with the posterior and lateral portions of the user's scrotum and testicles. The center section 12 of the insert 11 is aligned with the midsagittal plane of the user's body and the twin end sections 13 and 14 are tapered down from the center section 12 to be angled forward toward the front of the user's body and have sufficient length to be adjacent to the user's thighs. The insert 11 is positioned in the garment 15 so that it passes between the user's leg forward of the coronal plane of the user's body. This positioning allows the structure, to elevate the user's testicles forward and out from between the legs thus allowing the apparel to hold the testicles in place. A material covering is provided for the insert 11 to facilitate the ease of attaching the insert into the garment 13.

While I have described my invention in connection with specific embodiments thereof, it is clearly to be understood that this is down only by way of example and not as a limitation to the scope of my invention as set forth in the objects thereof and in the appended claims.

I claim:

1. A garment to be worn next to the skin of a male user's testicles, said garment comprising:
   a body portion for encircling said user's body trunk, said body portion having a front, a back and two sides;
   a crotch panel extending between said front and said back of said body portion for connecting them, said crotch panel and the sides of said body portion defining therebetween two leg openings, each of said openings being defined by a side edge of said crotch panel and the adjacent side of said body portion;
   a support means comprising a cushion secured to said crotch panel in such a position and extending in such a direction so that when worn by said user, said cushion extends inwardly of the garment from the crotch panel and upwardly therefrom for engaging a portion of said user's perineum and a portion of the rear of said user's scrotum for positioning the user's testicles away from a position from the user's legs.

2. The garment of claim 1, wherein said crotch panel comprises a fabric material.

3. The garment of claim 1, wherein said support means is connected to said crotch panel by adhesive.

4. The garment of claim 1, wherein said support means is connected to said crotch panel by a sewn seam.

5. The garment of claim 1, further comprising a covering material, wherein said cushion is covered by said covering material.

6. The garment of claim 1, wherein said cushion is crescent-shaped.

7. The garment of claim 6, wherein said crescent-shaped cushion includes a center section of a given thickness and twin end sections of less thickness than said center section.

8. The garment of claim 6, wherein said center section of said crescent-shaped cushion is aligned with a midsagittal plane of said body portion, said twin end sections are tapered in thickness from said center section and are angled forward from said center section toward the front of said body portion and having sufficient length to be adjacent to the user's legs.

9. The garment of claim 6, wherein said crescent-shaped cushion is made of a flexible foam material.

10. The garment of claim 8, wherein said crescent-shaped cushion is a flexible foam material.

* * * * *